(12) United States Patent
Huang et al.

(10) Patent No.: US 12,324,905 B2
(45) Date of Patent: Jun. 10, 2025

(54) NEEDLE COVER WITH UNDERCUT

(71) Applicant: Becton Dickinson France, Le Pont-de-Claix (FR)

(72) Inventors: Longxiang Huang, Jiangsu (CN); Bo Yan, Shanghai (CN); Jeremy Zucchelli, Saint martin d'hères (FR)

(73) Assignee: Becton Dickinson France, Le Pont-de-Claix (FR)

( * ) Notice: Subject to any disclaimer, the term of this patent is extended or adjusted under 35 U.S.C. 154(b) by 774 days.

(21) Appl. No.: 17/440,365

(22) PCT Filed: Apr. 24, 2020

(86) PCT No.: PCT/EP2020/061485
§ 371 (c)(1),
(2) Date: Sep. 17, 2021

(87) PCT Pub. No.: WO2020/216918
PCT Pub. Date: Oct. 29, 2020

(65) Prior Publication Data
US 2022/0184322 A1 Jun. 16, 2022

(30) Foreign Application Priority Data
Apr. 26, 2019 (EP) .................................. 19305540

(51) Int. Cl.
*A61M 5/32* (2006.01)

(52) U.S. Cl.
CPC ........ *A61M 5/3204* (2013.01); *A61M 5/3202* (2013.01); *A61M 5/3213* (2013.01)

(58) Field of Classification Search
CPC ......................... A61M 5/3202; A61M 5/3204
See application file for complete search history.

(56) References Cited

U.S. PATENT DOCUMENTS

| 2,864,364 | A | 12/1958 | Mizzy |
| 3,931,815 | A | 1/1976 | Takatsuki |
| 4,248,246 | A | 2/1981 | Ikeda |
| 4,317,446 | A | 3/1982 | Ambrosio et al. |
| 4,468,223 | A | 8/1984 | Minagawa et al. |
| 4,551,138 | A | 11/1985 | Shinohara |
| 4,573,977 | A | 3/1986 | Crawford |
| 4,735,311 | A | 4/1988 | Lowe et al. |
| 4,964,866 | A | 10/1990 | Szwarc |

(Continued)

FOREIGN PATENT DOCUMENTS

| CN | 105007969 B | 1/2018 |
| CN | 105007970 B | 5/2018 |

(Continued)

*Primary Examiner* — Emily L Schmidt
*Assistant Examiner* — Samuel J Marrison
(74) *Attorney, Agent, or Firm* — The Webb Law Firm

(57) ABSTRACT

A needle cover for protecting a needle mounted on a tip of a barrel of a medical injection device, may include an inner shield, and an outer shield surrounding at least partially the inner shield, and fixed to said inner shield, wherein the needle cover may include an outer shield including a body including a first open end, a second end, and a sidewall extending between the first end and the second end, the body defining a cavity to receive an inner shield therein, a first undercut defined adjacent the first open end of the body.

13 Claims, 5 Drawing Sheets

(56) References Cited

U.S. PATENT DOCUMENTS

| | | |
|---|---|---|
| 4,986,818 A | 1/1991 | Imbert et al. |
| 5,085,647 A | 2/1992 | Henderson et al. |
| 5,098,400 A | 3/1992 | Crouse et al. |
| 5,147,325 A | 9/1992 | Mitchell et al. |
| 5,217,025 A | 6/1993 | Okamura |
| 5,451,213 A | 9/1995 | Teicher et al. |
| 5,484,413 A | 1/1996 | Gevorgian |
| 5,505,705 A | 4/1996 | Galpin et al. |
| 5,709,659 A | 1/1998 | Bennwik et al. |
| 5,980,495 A | 11/1999 | Heinz et al. |
| 6,015,396 A | 1/2000 | Buttgen et al. |
| 6,355,017 B2 | 3/2002 | Buttgen et al. |
| 6,485,474 B1 | 11/2002 | Heinz et al. |
| 6,544,233 B1 | 4/2003 | Fukui et al. |
| 6,551,286 B1 | 4/2003 | Claessens |
| 6,695,819 B2 | 2/2004 | Kobayashi |
| 6,719,732 B2 | 4/2004 | Courteix |
| 7,094,223 B2 | 8/2006 | Brunel |
| 7,331,941 B2 | 2/2008 | Vetter et al. |
| 7,387,617 B2 | 6/2008 | Wittland et al. |
| 7,559,919 B2 | 7/2009 | Pech et al. |
| 7,641,636 B2 | 1/2010 | Moesli et al. |
| 7,722,572 B2 | 5/2010 | Sprinkle et al. |
| 7,771,368 B2 | 8/2010 | Nakamura et al. |
| 8,057,441 B2 | 11/2011 | Tsubota |
| 8,096,977 B2 | 1/2012 | Ayiyama et al. |
| 8,123,724 B2 | 2/2012 | Gillespie, III |
| 8,277,421 B2 | 10/2012 | Koyama et al. |
| 8,372,105 B2 | 2/2013 | Nishiuchi et al. |
| 8,425,468 B2 | 4/2013 | Weston |
| 8,460,212 B2 | 6/2013 | Nakamura et al. |
| 8,469,985 B2 | 6/2013 | Nishiuchi |
| 8,512,295 B2 | 8/2013 | Evans et al. |
| 8,657,780 B2 | 2/2014 | Palmer-Felgate |
| 8,672,894 B2 | 3/2014 | Bonnet |
| 8,734,402 B2 | 5/2014 | Sharp et al. |
| 8,747,357 B2 | 6/2014 | Stamp et al. |
| 8,771,235 B2 | 7/2014 | Chevallier et al. |
| 8,858,507 B2 | 10/2014 | Nielsen et al. |
| 8,858,508 B2 | 10/2014 | Lavi et al. |
| 8,900,197 B2 | 12/2014 | Crow |
| 8,913,123 B2 | 12/2014 | Miller |
| 8,961,460 B2 | 2/2015 | Yokota et al. |
| 9,084,854 B2 | 7/2015 | Evans et al. |
| 9,132,266 B2 | 9/2015 | Hayakawa et al. |
| 9,192,729 B2 | 11/2015 | Iwase et al. |
| 9,248,245 B2 | 2/2016 | Ekman et al. |
| 9,278,179 B2 | 3/2016 | Schoonmaker |
| 9,295,785 B2 | 3/2016 | Ekman et al. |
| 9,302,053 B2 | 4/2016 | Holmqvist |
| 9,314,574 B2 | 4/2016 | Roberts et al. |
| 9,333,305 B2 | 5/2016 | McLoughlin et al. |
| 9,339,600 B2 | 5/2016 | Weston |
| 9,339,610 B2 | 5/2016 | Julian et al. |
| 9,352,099 B2 | 5/2016 | Roberts et al. |
| 9,415,176 B1 | 8/2016 | Benson et al. |
| 9,468,724 B2 | 10/2016 | Evans et al. |
| 9,468,726 B2 | 10/2016 | Lundquist |
| 9,545,484 B2 | 1/2017 | Bicknell et al. |
| 9,545,485 B2 | 1/2017 | Takemoto |
| 9,757,526 B2 | 9/2017 | Iwase et al. |
| 9,808,584 B2 | 11/2017 | Takemoto |
| 9,839,752 B2 | 12/2017 | Fournier et al. |
| 9,861,761 B2 | 1/2018 | Gonzales et al. |
| 9,867,950 B2 | 1/2018 | Takemoto |
| 9,919,107 B2 | 3/2018 | Imai et al. |
| 9,919,109 B2 | 3/2018 | Arinobe et al. |
| 9,925,327 B2 | 3/2018 | Okihara et al. |
| RE46,789 E | 4/2018 | Olson |
| 9,950,124 B2 | 4/2018 | Imai et al. |
| 9,962,497 B2 | 5/2018 | Takemoto |
| 9,962,498 B2 | 5/2018 | Horita et al. |
| 10,369,289 B2 | 8/2019 | Cabiri et al. |
| 10,537,688 B2 | 1/2020 | Wittland et al. |
| 10,653,848 B2 | 5/2020 | Wittland et al. |
| 11,040,148 B2 | 6/2021 | Swal et al. |
| 11,305,062 B2 | 4/2022 | Fabien et al. |
| 2004/0186440 A1 | 9/2004 | Jansen et al. |
| 2005/0215952 A1 | 9/2005 | Brunel et al. |
| 2006/0212021 A1 | 9/2006 | Yazaki et al. |
| 2007/0250016 A1 | 10/2007 | Pech et al. |
| 2008/0183140 A1 | 7/2008 | Paproski et al. |
| 2008/0215013 A1 | 9/2008 | Felix-Faure |
| 2008/0269690 A1 | 10/2008 | Felix-Faure |
| 2009/0118678 A1 | 5/2009 | Kawashima |
| 2009/0124981 A1 | 5/2009 | Evans |
| 2010/0145227 A1 | 6/2010 | Wessel |
| 2011/0118568 A1 | 5/2011 | Sei |
| 2011/0202035 A1 | 8/2011 | Voellmicke et al. |
| 2012/0179109 A1 | 7/2012 | Takemoto et al. |
| 2012/0191048 A1 | 7/2012 | Eaton |
| 2012/0238961 A1* | 9/2012 | Julian ............... A61M 5/20 29/700 |
| 2012/0330243 A1 | 12/2012 | Liversidge |
| 2013/0012886 A1 | 1/2013 | Kawachi |
| 2013/0030365 A1 | 1/2013 | Liversidge |
| 2013/0053788 A1 | 2/2013 | Dugand et al. |
| 2013/0072882 A1 | 3/2013 | Ogawa et al. |
| 2013/0123711 A1 | 5/2013 | Schoonmaker et al. |
| 2013/0174518 A1 | 7/2013 | Tachikawa et al. |
| 2013/0204197 A1 | 8/2013 | Bicknell et al. |
| 2013/0261563 A1* | 10/2013 | Zachek ............ A61M 5/3213 604/263 |
| 2013/0274677 A1 | 10/2013 | Ekman et al. |
| 2013/0296801 A1 | 11/2013 | Takemoto et al. |
| 2014/0025013 A1 | 1/2014 | Dowds et al. |
| 2014/0107577 A1 | 4/2014 | Boyd et al. |
| 2014/0221873 A1 | 8/2014 | Hayakawa et al. |
| 2014/0236102 A1 | 8/2014 | Matsumoto et al. |
| 2014/0249479 A1 | 9/2014 | Pfrang |
| 2014/0343503 A1* | 11/2014 | Holmqvist ......... A61M 5/3204 81/3.4 |
| 2015/0174329 A1 | 6/2015 | Takemoto |
| 2015/0190566 A1 | 7/2015 | Okihara |
| 2015/0196720 A1 | 7/2015 | Okihara et al. |
| 2015/0217061 A1 | 8/2015 | Sadowski et al. |
| 2015/0258283 A1 | 9/2015 | Imai et al. |
| 2015/0297837 A1 | 10/2015 | Schraga |
| 2015/0335830 A1 | 11/2015 | Horita et al. |
| 2015/0352291 A1 | 12/2015 | Fournier et al. |
| 2016/0001006 A1 | 1/2016 | Takemoto et al. |
| 2016/0001013 A1 | 1/2016 | Fournier et al. |
| 2016/0001015 A1 | 1/2016 | Kucuk et al. |
| 2016/0008553 A1 | 1/2016 | Fournier et al. |
| 2016/0015905 A1 | 1/2016 | Fournier et al. |
| 2016/0106929 A1 | 4/2016 | Fournier et al. |
| 2016/0175539 A1 | 6/2016 | Riedel et al. |
| 2016/0206829 A1 | 7/2016 | Protasiewicz et al. |
| 2016/0220766 A1 | 8/2016 | Kawano et al. |
| 2016/0243305 A1 | 8/2016 | Nakamura et al. |
| 2016/0243315 A1 | 8/2016 | Perche et al. |
| 2016/0271338 A1 | 9/2016 | Fournier et al. |
| 2016/0271848 A1 | 9/2016 | Takemoto et al. |
| 2016/0287810 A1 | 10/2016 | Keim et al. |
| 2016/0296713 A1 | 10/2016 | Schader et al. |
| 2016/0310676 A1 | 10/2016 | Darras et al. |
| 2016/0325051 A1 | 11/2016 | Keim et al. |
| 2016/0331904 A1 | 11/2016 | Huthmacher et al. |
| 2016/0331908 A1 | 11/2016 | Bode |
| 2016/0354550 A1 | 12/2016 | Ward et al. |
| 2016/0354551 A1 | 12/2016 | Keim et al. |
| 2016/0354552 A1 | 12/2016 | Keim et al. |
| 2016/0367756 A1 | 12/2016 | Felts et al. |
| 2017/0014578 A1 | 1/2017 | Bunch |
| 2017/0021103 A1 | 1/2017 | Mosebach et al. |
| 2017/0080159 A1 | 3/2017 | Wei |
| 2017/0143893 A1 | 5/2017 | Hasumi et al. |
| 2017/0182259 A1 | 6/2017 | Fukushi et al. |
| 2017/0189603 A1 | 7/2017 | Okihara et al. |
| 2017/0197040 A1 | 7/2017 | Funatsu et al. |
| 2017/0203052 A1 | 7/2017 | Abe et al. |
| 2017/0224932 A1 | 8/2017 | Fournier et al. |
| 2017/0274151 A1 | 9/2017 | Allen |
| 2017/0326306 A1 | 11/2017 | Grosser |

(56) References Cited

U.S. PATENT DOCUMENTS

| | | |
|---|---|---|
| 2017/0361030 A1 | 12/2017 | Moore |
| 2018/0011417 A1 | 1/2018 | Shimizu et al. |
| 2018/0015229 A1 | 1/2018 | Iwase |
| 2018/0015230 A1 | 1/2018 | Okihara |
| 2018/0028762 A1 | 2/2018 | Maxfield |
| 2018/0064885 A1 | 3/2018 | Yamazaki et al. |
| 2018/0085534 A1 | 3/2018 | Gonzales et al. |
| 2018/0104421 A1 | 4/2018 | Wittland et al. |
| 2018/0110934 A1 | 4/2018 | Wittland et al. |
| 2018/0140783 A1* | 5/2018 | Raday ................. A61M 5/3257 |
| 2018/0161511 A1 | 6/2018 | Fraas et al. |
| 2018/0272075 A1 | 9/2018 | Stefanov et al. |
| 2018/0304030 A1 | 10/2018 | Julian et al. |
| 2018/0311442 A1 | 11/2018 | Saussaye et al. |
| 2018/0353702 A1* | 12/2018 | Jugl .................... A61M 5/3202 |
| 2019/0201634 A1* | 7/2019 | Newton .............. A61M 5/3213 |
| 2020/0061302 A1* | 2/2020 | Alexandersson . A61M 5/31571 |
| 2021/0220565 A1* | 7/2021 | Frost ................... A61M 5/3204 |

FOREIGN PATENT DOCUMENTS

| | | |
|---|---|---|
| DE | 10316127 A1 | 11/2004 |
| DE | 102011014200 B4 | 2/2014 |
| DE | 102011017275 B4 | 4/2014 |
| DE | 102013112654 A1 | 5/2015 |
| EC | SP077339 A | 4/2007 |
| EP | 0498737 B1 | 7/1995 |
| EP | 2172238 A1 | 4/2010 |
| EP | 2548596 A1 | 1/2013 |
| EP | 3325054 B1 | 3/2021 |
| FR | 2777787 B1 | 4/2001 |
| FR | 3003469 B1 | 4/2016 |
| GB | 1235347 A | 6/1971 |
| IL | 249004 A | 1/2021 |
| IL | 257906 A | 1/2022 |
| JP | S5519160 A | 2/1980 |
| JP | H01212563 A | 8/1989 |
| JP | 200754194 A | 3/2007 |
| JP | 6042816 B2 | 12/2016 |
| KR | 1020180006383 A | 1/2018 |
| WO | 8900830 A1 | 2/1989 |
| WO | 8908468 A1 | 9/1989 |
| WO | 2007082226 A1 | 7/2007 |
| WO | 2008016710 A1 | 2/2008 |
| WO | 2008041437 A1 | 4/2008 |
| WO | 2009104765 A1 | 8/2009 |
| WO | 2011068130 A1 | 6/2011 |
| WO | 2011068131 A1 | 6/2011 |
| WO | 2011122393 A1 | 10/2011 |
| WO | 2011122395 A1 | 10/2011 |
| WO | 2011125475 A1 | 10/2011 |
| WO | 2011125561 A1 | 10/2011 |
| WO | 2012082818 A3 | 6/2012 |
| WO | 2012133267 A1 | 10/2012 |
| WO | 2013046857 A1 | 4/2013 |
| WO | 2013047149 A1 | 4/2013 |
| WO | 2013145998 A1 | 10/2013 |
| WO | 2013146000 A1 | 10/2013 |
| WO | 2013146099 A1 | 10/2013 |
| WO | 2013146215 A1 | 10/2013 |
| WO | 2013172104 A1 | 11/2013 |
| WO | 2013183464 A1 | 12/2013 |
| WO | 2013190941 A1 | 12/2013 |
| WO | 2014033873 A1 | 3/2014 |
| WO | 2014049797 A1 | 4/2014 |
| WO | 2014115241 A1 | 7/2014 |
| WO | 2014162439 A1 | 10/2014 |
| WO | 2014184932 A1 | 11/2014 |
| WO | 2015001819 A1 | 1/2015 |
| WO | 2015029628 A1 | 3/2015 |
| WO | 2015049945 A1 | 4/2015 |
| WO | 2015105511 A1 | 7/2015 |
| WO | 2015110533 A2 | 7/2015 |
| WO | 2015147018 A1 | 10/2015 |
| WO | 2016202498 A1 | 12/2016 |
| WO | 2016202670 A1 | 12/2016 |
| WO | 2017051108 A1 | 3/2017 |
| WO | 2017051113 A1 | 3/2017 |
| WO | 2017062938 A1 | 4/2017 |
| WO | 2017081421 A1 | 5/2017 |
| WO | 2018011417 A1 | 1/2018 |
| WO | 2018172853 A1 | 9/2018 |
| WO | 2019074788 A1 | 4/2019 |

* cited by examiner

NEEDLE COVER WITH UNDERCUT

CROSS-REFERENCE TO RELATED APPLICATIONS

This application is the United States national phase of International Application No. PCT/EP2020/061485 filed Apr. 24, 2020, and claims priority to Europe Patent Application No. 19305540.7 filed Apr. 26, 2019, the entire disclosures of which are hereby incorporated by reference in their entirety.

BACKGROUND OF THE INVENTION

Field of the Invention

The present disclosure relates generally to medical injection devices for delivery of a fluid or liquid medicament. More particularly, the present disclosure relates to a needle cover adapted to be mounted on a tip of a medical injection device for covering a needle attached thereon. The disclosure also relates to a medical assembly including a medical injection device and a needle cover for enclosing the needle of the medical injection device.

Description of Related Art

Medical injection devices such as syringes are well known in the art. These devices typically include a container for containing a medical composition such as a liquid medicament. Said container usually includes an end piece in a form of a longitudinal tip defining a fluid path through which the medical solution is expelled. A needle may be attached to the tip in order to prick the patient's skin and to perform the injection of the medical composition.

In order to maintain sterility prior to use and to reduce the risk of incurring an accidental needle-stick, protection of the needle is important. Thus, a needle cover may be mounted on the tip of the barrel so as to enclose the needle. This renders the needle physically inaccessible by the persons around the device. The needle cover may include an inner shield, in a material with elastomeric properties, and may further include an outer shield, in rigid plastic, surrounding the inner shield. The inner needle shield ensures the sealing of the medical injection device. To that purpose, the inner needle shield includes a sealing portion that sealingly contacts the outer surface of the syringe's tip to provide a tight seal. The inner needle shield prevents any contamination of the medical composition from the outside environment, thereby assuring the container closure integrity. The inner needle shield further prevents any leakage of composition from the outlet of the needle to the external environment. To that purpose, the needle is preferably pricked in the inner needle shield.

Immediately prior to use, the user must remove the protective needle cover from the medical injection device. The force needed to remove a needle cover is measured by a physical parameter called "pull out force" (also referred to as "POF"). The pull out force necessary for removing the known needle covers from an injection device, such as a syringe, may be quite high and is due in particular to the pressure exerted onto the tip by the inner needle shield which results in friction between the inner needle shield and the tip.

As a consequence, a user having a reduced strength, for example weakened by a disease, may not be able to remove the needle shield and use the injection device for his treatment.

Moreover, healthcare professional who often use injection devices, such as nurses, have a high risk of injuring themselves, since they may not control the force they apply for pulling off the needle cover from the injection device, which may result in uncontrolled and dangerous movements. Lastly, the needle of the syringe may be bent during the removing of the needle shield because of this high required pull out force.

SUMMARY OF THE INVENTION

In view of the problems identified above, there is a current need for a needle cover that allows reducing the pull out force needed for removing said needle cover from a medical injection device, and that does not decrease the tight sealing of said needle cover to the tip of the medical injection device (while keeping intact the no leakage property of the needle cover).

In one example of the present disclosure, a needle cover for protecting a needle mounted on a tip of a barrel of a medical injection device, wherein the tip extends from a distal end of the barrel, may include an inner shield extending along a longitudinal axis, including an inner proximal connection element configured to sealingly contact the tip of the barrel, and an outer shield surrounding at least partially the inner shield, and fixed to said inner shield, wherein said outer shield of the needle cover may include a body including a first open end, a second end, and a sidewall extending between the first end and the second end, the body defining a cavity to receive an inner shield therein, and an undercut defined adjacent the first open end of the body.

In another example of the present disclosure, the outer shield of the needle cover further comprises a second undercut defined adjacent the first open end of the body, wherein a longitudinal length of the first undercut extending from the first open end towards the second end is less than a longitudinal length of the second undercut extending from the first open end towards the second end.

In another example of the present disclosure, a distance from the first open end of the outer shield to a proximal edge of the first undercut present on the body of the outer shield is greater than a distance from the first open end of the outer shield to a proximal edge of the second undercut present on the body of the outer shield. A first latching tab may extend from an inner surface of the body of the outer shield proximate the first undercut, and a second latching tab may extend from the inner surface of the body of the outer shield proximate the second undercut. The first latching tab may have a circumferential width that is greater than a circumferential width of the second latching tab. The first and second latching tabs may include a proximal angled surface. A difference between a distance from the first open end of the outer shield to a proximal edge of the first undercut and a distance from the first open end of the outer shield to a proximal edge of the second undercut may be at least 1 millimeter. The first and second undercuts may be diametrically opposed to one another. The first and second undercuts may be rectangular in shape.

Moreover, the body may define at least one U-shaped groove on an outer surface thereof. The U-shaped groove may include a distal wall and a proximal wall that extend radially from the body. A distance from the first open end of the outer shield to a distal edge of the first undercut may be equal to a distance from the first open end of the outer shield to a distal edge of the second undercut.

In another example of the present disclosure, a medical assembly, comprising: a medical injection device, comprising: a barrel defining a reservoir adapted to contain a medical composition; a tip extending from a distal face of the barrel, defining a fluid path extending through the tip and in fluid communication with the reservoir, a needle being in communication with the reservoir; and a needle cover adapted to cover the needle; characterized in that: the needle cover comprises: an inner shield extending along a longitudinal axis, comprising an inner proximal connection element configured to sealingly contact the tip of the barrel; and an outer shield covering at least a portion of the inner shield, the outer shield comprising: a body including a first open end, a second end, and a sidewall extending between the first end and the second end, the body defining a cavity to receive the inner shield therein; and a first undercut defined adjacent the first open end of the body.

Advantageously, the outer shield of the medical assembly further comprises a second undercut distinct from the first undercut and defined adjacent the first open end of the body, wherein a longitudinal length of the first undercut extending from the first open end of the outer shield towards the second end of the outer shield is less than a longitudinal length of the second undercut extending from the first open end of the outer shield towards the second end of the outer shield.

The following clauses also are directed to the present invention and disclosure:

Clause 1: A needle cover for protecting a needle mounted on a tip of a barrel of a medical injection device, wherein the tip extends from a distal end of the barrel, the needle cover comprising: an inner shield extending along a longitudinal axis, comprising an inner proximal connection element configured to sealingly contact the tip of the barrel, and an outer shield surrounding at least partially the inner shield, and fixed to said inner shield, wherein the outer shield comprises a body including a first open end, a second end, and a sidewall extending between the first end and the second end, the body defining a cavity to receive an inner shield therein; and a first undercut defined adjacent the first open end of the body.

Clause 2: The needle cover of Clause 1, wherein the body of the outer shield further comprises a second undercut defined adjacent the first open end of the body, wherein a longitudinal length of the first undercut extending from the first open end of the outer shield towards the second end is less than a longitudinal length of the second undercut extending from the first open end of the outer shield towards the second end.

Clause 3: The needle cover of Clause 2, wherein a distance from the first open end to a proximal edge of the first undercut is greater than a distance from the first open end to a proximal edge of the second undercut.

Clause 4: The needle cover of Clause 2, further comprising: a first latching tab that extends from an inner surface of the body proximate the first undercut; and a second latching tab that extends from the inner surface of the body proximate the second undercut.

Clause 5: The needle cover of Clause 4, wherein the first latching tab has a circumferential width that is greater than a circumferential width of the second latching tab.

Clause 6: The needle cover of Clause 4, wherein the first and second latching tabs comprise a proximal angled surface.

Clause 7: The needle cover of Clause 2, wherein a difference between a distance from the first open end to a proximal edge of the first undercut and a distance from the first open end to a proximal edge of the second undercut is at least 1 millimeter.

Clause 8: The needle cover of Clause 2, wherein the first and second undercuts are diametrically opposed to one another.

Clause 9: The needle cover of Clause 2, wherein the first and second undercuts are rectangular in shape.

Clause 10: The needle cover of Clause 1, wherein the body defines at least one U-shaped groove on an outer surface thereof.

Clause 11: The needle cover of Clause 10, wherein the U-shaped groove comprises a distal wall and a proximal wall that extend radially from the body.

Clause 12: The needle cover of Clause 2, wherein a distance from the first open end to a distal edge of the first undercut is equal to a distance from the first open end to a distal edge of the second undercut.

Clause 13: The needle cover of Clause 2, wherein the outer shield is fixed to the inner shield by a snap-fit connection, the inner proximal connection element of the inner shield is inserted in the first and second undercuts of the outer shield to form the snap-fit connection so that, when a pulling force is applied to the outer shield in a distal direction, the inner shield makes a first contact with end surface of the first undercut and then with an end surface of the second undercut, thereby flexing the inner shield in a radial direction to assist disengagement of the inner shield from the tip.

Clause 14: A medical assembly, comprising: a medical injection device, comprising: a barrel defining a reservoir adapted to contain a medical composition; a tip extending from a distal face of the barrel, defining a fluid path extending through the tip and in fluid communication with the reservoir, a needle in communication with the reservoir; and a needle cover of any of Clauses 1 to 12 and adapted to cover the needle; characterized in that: the needle cover comprises: an inner shield extending along a longitudinal axis, comprising an inner proximal connection element configured to sealingly contact the tip of the barrel; and an outer shield covering at least a portion of the inner shield, the outer shield comprising: a body including a first open end, a second end, and a sidewall extending between the first end and the second end, the body defining a cavity to receive the inner shield therein; and a first undercut defined adjacent the first open end of the body.

Clause 15: The medical assembly of Clause 14, wherein the barrel and the tip of the medical injection device are made of glass.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DESCRIPTION OF THE INVENTION

Figure 1:
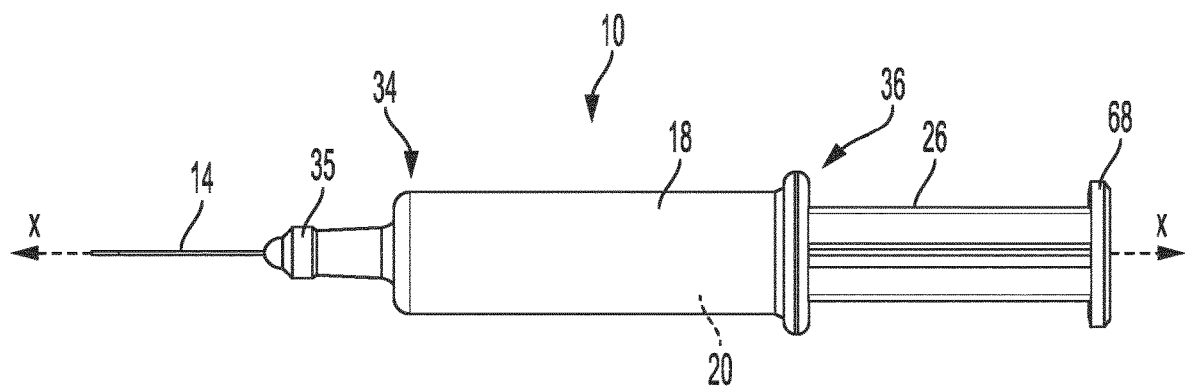
FIG. 1 is a perspective view of a medical injection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a medical injection device adapted for contact with a patient's skin, and "proximal" refers to the opposite direction of distal, i.e., away from the end of a medical injection device. In other words, the "distal direction" is to be understood as meaning the direction of injection. The distal direction corresponds to the travel direction of the plunger during the injection, the medical composition contained initially in the barrel being expelled from the latter. The "proximal direction" is to be understood as meaning the opposite direction to said direction of injection. For purposes of this disclosure, the above-mentioned references are used in the description of the components of a medical injection device in accordance with the present disclosure.

Referring to FIG. 1, the medical injection device 10 includes a barrel 18 extending along a longitudinal axis X from a proximal face 36 to a distal face 34, defining a reservoir 20 for a medical composition such as a liquid medicament. The medical injection device 10 may also include a stopper (not shown), and a plunger rod 26 having a flange 68 and translationally movable inside the barrel 18 from a proximal position to a distal position for injecting the composition.

The medical injection device 10 further includes a distal tip 35 extending along the axis X from the distal face 34 of the barrel 18. The distal tip 35 is at least partially hollow so as to form a fluid path in fluidic communication with the barrel 18. A needle 14 may be attached to the distal tip 35 of the injection device 10 and is in fluid communication with the fluid path. It is noted herein that the distal face 34 of the barrel 18 is proximate the shoulder of the medical injection device.

The medical injection device 10 is preferably made of glass, and more preferably is a glass syringe. Such glass syringes are largely used in hospital environments and readily sterilizable. The medical injection device 10 is preferably a prefilled syringe. The medical injection device 10 is more preferably a syringe with a staked needle.

Figure 2:
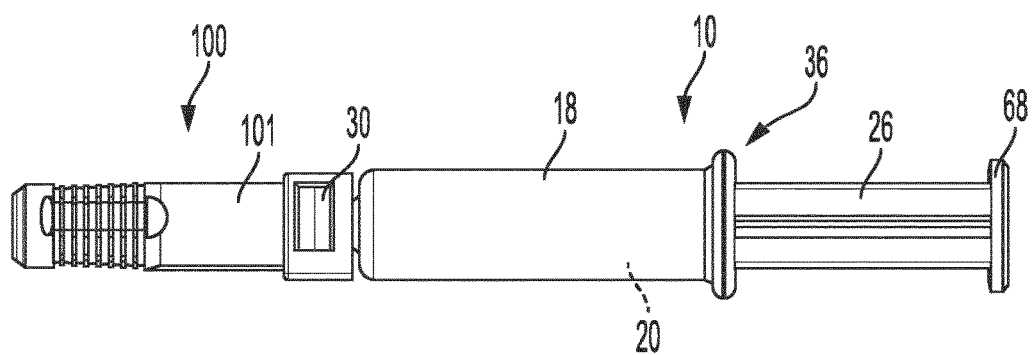
FIG. 2 is a perspective view of the medical injection device of FIG. 1 with a needle cover in accordance with an embodiment of the present invention.

Referring to FIG. 2, the medical injection device further includes a needle cover 100. The needle cover 100 shields and covers the needle 14. The needle cover 100 may include an outer shield 101 and an inner shield 30 that covers the needle 14 and is covered by the outer shield 101.

Figure 3:
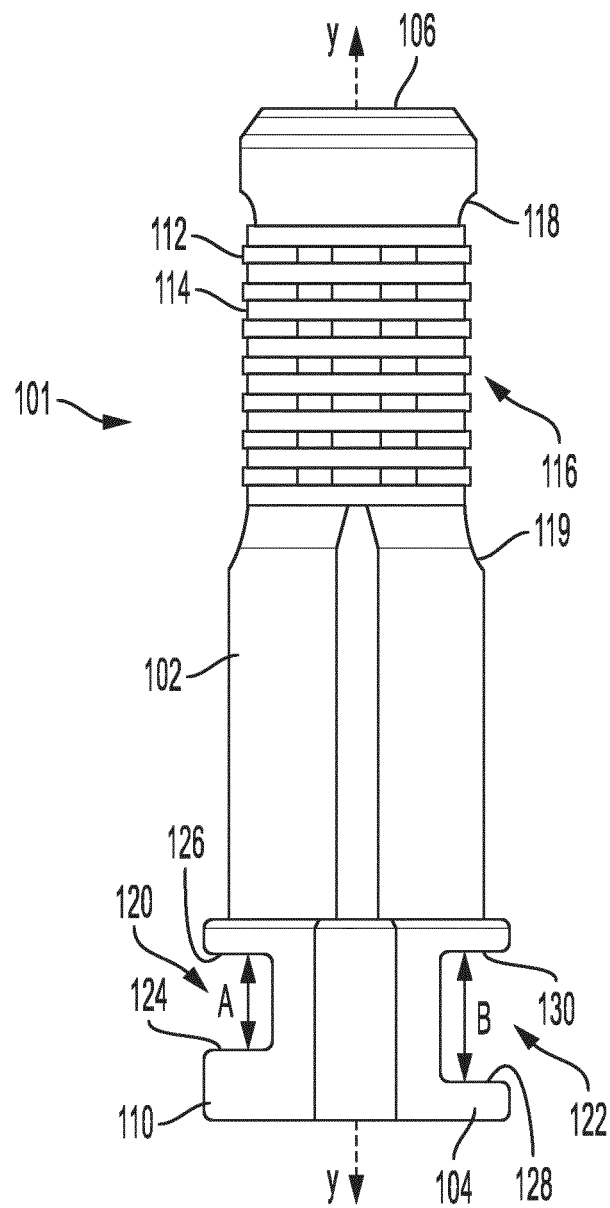
FIG. 3 is a front view of a needle cover in accordance with an embodiment of the present invention.

Referring to FIG. 3, the outer shield 101 in accordance with an embodiment of the present invention is described in greater detail. The outer shield 101 is preferably made in a rigid material, such as rigid plastic. The outer shield 101 may be made of a medical grade plastic. The rigid material confers rigidity to the outer shield 101, which allows said outer shield 101 to better protect the needle cover 100 from shocks. The structural integrity of the needle cover 100 is thereby improved.

The outer shield 101 includes a body 102 having a proximal end 104 and a distal end 106. Said body 102 extends along a longitudinal axis Y. Said axis Y coincides with the axis X when the needle cover 100 is mounted on the tip 35 of the medical injection device 10.

In one example, the body 102 may be substantially cylindrical in shape. The body 102 may define an inner cavity 108 (see FIG. 6) that at least partially receives the inner shield 30 of the medical injection device 10. A collar 110 may be formed on the proximal end 104 of the outer shield 101. The collar 110 may have a larger diameter than the remaining portion of the body 102. In one example, a plurality of ribs and grooves 112, 114 may be defined on the body 102 of the outer shield 101. The ribs and grooves 112, 114 may be provided adjacent the distal end 106 of the outer shield 101. The ribs and grooves 112, 114 provide a gripping surface for a user to use when pulling the outer shield 101 away from the medical injection device 10.

Figure 4:
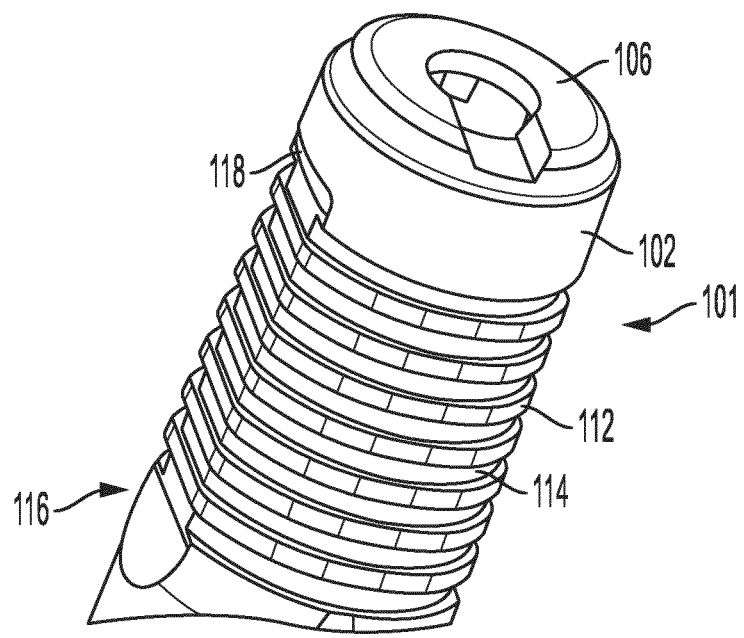
FIG. 4 is an isolated perspective view of the needle cover of FIG. 3.

In another example shown in FIGS. 3 and 4, a U-shaped groove 116 may be formed in a side surface of the body 102 to create another feature to assist a user in pulling the outer shield 101 away from the medical injection device 10. The U-shaped groove 116 includes a distal wall 118 and a proximal wall 119. The distal wall 118 of the U-shaped groove 116 allows a user to apply pressure against the outer shield 101 to create a greater pulling force to pull the outer shield 101 away from the medical injection device 10. The plurality of ribs and grooves 112, 114 may be provided along said U-shaped groove 116.

Figure 5:
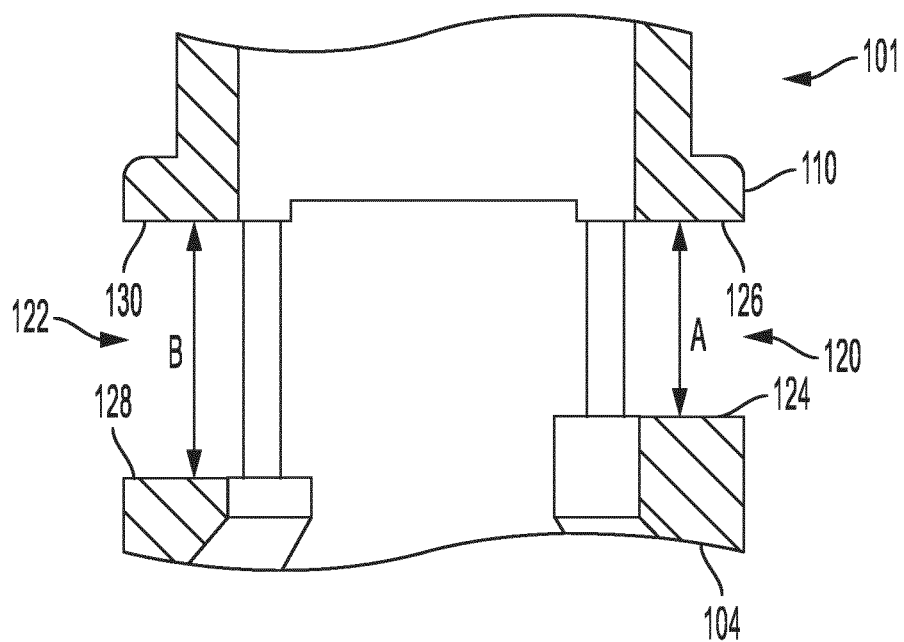
FIG. 5 is a cross-sectional view of a proximal portion of the needle cover of FIG. 3.

With reference to FIG. 5, the collar 110 of the body 102 of the outer shield 101 may define at least one undercut, preferably at least a pair of undercuts 120, 122. In one example, the undercuts 120, 122 are apertures that extend through the outer shield 101. The presence of the undercuts 120, 122 allows reducing the pull-out force required by a user to remove the outer shield 101 from the medical injection device 10, as discussed herein. The undercuts 120, 122 may also be referred to as "windows" that extend through the collar 110. Indeed, thanks to these windows, the user can visually ensure that the inner shield 30 is at least partially enclosed in the outer shield 101.

In one example, at least one of the undercuts 120, 122, preferably both undercuts 120, 122, may be substantially rectangular in shape. In one example, the undercuts 120, 122 may be diametrically opposed from one another on the collar 110. A longitudinal length A of the first undercut 120 may be less than a longitudinal length B of the second undercut 122. The longitudinal length A may be measured from a proximal surface 124 of the first undercut 120 to a distal surface 126 of the first undercut 120. The longitudinal length B may be measured from a proximal surface 128 of the second undercut 122 to a distal surface 130 of the second undercut 122. In another example, the distance from the proximal end 104 of the body 102 to the distal surface 126 of the first undercut 120 is substantially equal to a distance from the proximal end 104 of the body 102 to the distal surface 130 of the second undercut 122. When the longitudinal lengths A, B of the undercuts 120, 122 are different from one another, the undercuts 120, 122 are considered asymmetric from one another. In another example, a distance from the proximal end 104 of the body 102 to the proximal surface 124 of the first undercut 120 is greater than a distance from the proximal end 104 of the body 102 to the proximal surface 128 of the second undercut 122. In one example, the undercuts 120, 122 are extruded from the collar 110 of the body 102. It is also contemplated that any other manufacturing methods may be used to define the undercuts 120, 122 in the collar 110. Advantageously, the two undercuts 120, 122 are distinct from each other and define two different apertures in the collar 110.

Figure 6:
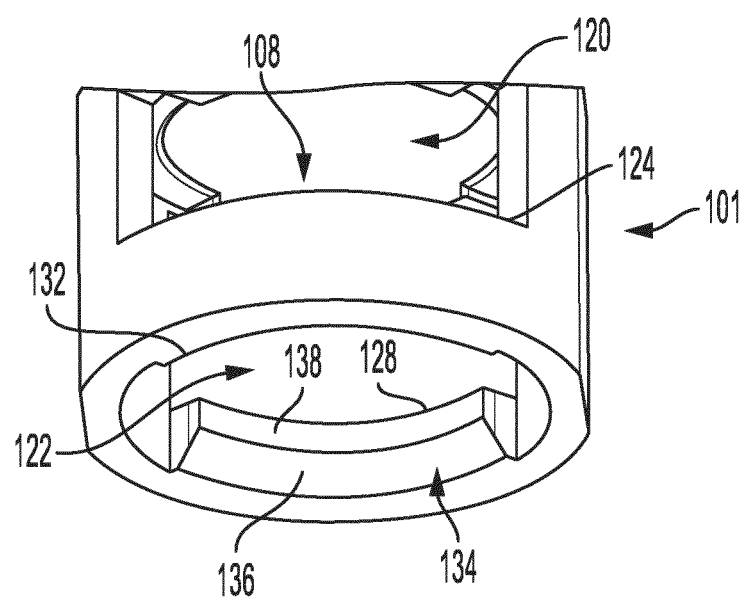
FIG. 6 is an isolated perspective view of the proximal portion of the needle cover of FIG. 3.

With reference to FIG. 6, another feature of the outer shield 101 is described in detail. In particular, two latching tabs 132, 134 may inwardly extend from an inner surface of the collar 110 near the proximal end 104 of the body 102. The latching tabs 132, 134 may include an inclined surface 136 that is angled relative to the longitudinal axis Y of the outer shield 101, and a substantially planar surface 138 that extends parallel to a longitudinal axis Y of the outer shield 101. The latching tabs 132, 134 may assist in the insertion of the inner shield 30 into the inner cavity 108 of the outer shield 101. In one example, a circumferential width of one latching tab 134 is greater than a circumferential width of the other latching tab 132.

Figure 7:
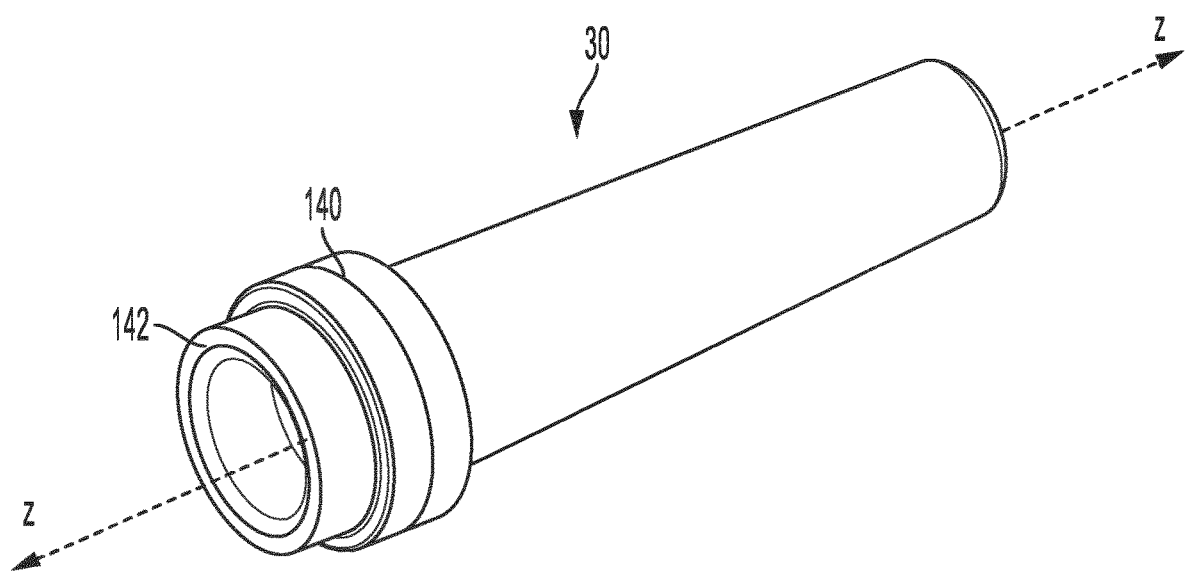
FIG. 7 is a perspective view of an inner shield in accordance with an embodiment of the present invention.

With reference to FIG. 7, the inner shield 30 that may be used in the invention is represented. Said inner shield 30 extends along a longitudinal axis Z. Said axis Z coincides with the axis Y when the inner shield 30 is at least partly enclosed in the outer shield 101. The inner shield 30 preferably has a cylindrical shape and a circular cross section. Advantageously, the inner shield 30 includes an inner proximal connection part 140 configured to sealingly engage the tip 35 of the injection device 10, as shown in FIG. 1. The inner proximal connection part 140 has preferably a larger diameter that the rest of the inner shield 30. Said inner proximal connection part 140 may be shaped as a circumferential flange. The inner proximal connection part 140 is thus easier to distinguish from the rest of the body and the fixation of the inner shield 30 to the outer shield 101 is improved as described in the following.

The inner shield 30 is preferably made in a material with elastomeric properties. In this way, the inner proximal connection part 140 may slightly deform when connecting the inner shield 30 to the injection device 10 so as to match the shape of the tip 35. Meanwhile, the needle tip, or distal part of the needle 14, may penetrate the inner shield 30. This further reduces the risk of leakage of the medical composition via the needle 14 to the external environment. The material with elastomeric properties is preferably a thermoplastic elastomer, an elastomer, or a rubber. Preferably, the material with elastomeric properties is sterilizable.

In one embodiment, the outer shield 101 surrounds at least partially the inner shield 30. The outer needle shield 101 is fixed to the inner needle shield 30. To this end, the inner proximal connection part 140 of the inner shield 30 is partially inserted in the two undercuts 120, 122, in a snap-fit connection. The inner proximal connection part 140 of the inner shield 30 abuts both the proximal surfaces 124, 128 and the distal surfaces 126, 130 of both the undercuts 120, 122, thereby preventing any translational movement of the inner shield 30 along the axis Y relative to the outer shield 101. Advantageously, the inner proximal connection part 140 also abuts the side surfaces of the undercuts 120, 122, thereby preventing any rotational movement of the inner shield 30 around the axis Y relative to the outer needle shield 101.

The inner shield 30 and the outer shield 101 may be fixed together by other fixing means than the snap-fit connection of the undercuts 120, 122, and the inner proximal connection part 140 or in addition to said snap-fit connection. When the needle cover 100 is mounted on the injection device 10, the inner shield 30 encloses at least a portion of the tip 35 of the barrel 18, and the proximal connection part 140 firmly contacts a proximal portion of the tip 35. The needle cover 100 is thus tightly and sealingly connected to the tip 35.

In order to mount the needle cover 100 on the syringe, the outer shield 101 is firstly placed over the inner shield 30, and then the entire needle cover 100 is mounted on the syringe. As previously described, when the inner shield 30 and the outer shield 101 are fixed together, the proximal connection part 140 of the inner shield 30 will be locked into the undercuts 120, 122 defined in the collar 110 of the outer shield 101. Once locked into the undercuts 120, 122, the proximal connection part 140 is prevented from moving in a distal direction due to the distal surfaces 126, 130 of the undercuts 120, 122 and is prevented from moving in a proximal direction due to the proximal surfaces 124, 128 of the undercuts 120, 122.

After the needle cover 100 has been positioned on the medical injection device 10, the needle cover 100 can be moved in a distal direction to remove it from the medical injection device 10. As a pulling force is applied to the outer shield 101 by a user, the outer shield 101 is moved in the distal direction along with the inner shield 30. As the outer shield 101 is moved in the distal direction, the proximal surface 124 of the first undercut 120 will begin to contact and abut the proximal connection part 140 of the inner shield 30. Once the proximal surface 124 of the undercut 120 contacts the proximal connection part 140, the proximal surface 124 begins to push the proximal connection part 140 in a distal direction. As the proximal connection part 140 is pushed in the distal direction, the proximal connection part 140 begins to flex such that a collar 142 of the inner shield 30 is pulled in a radial direction away from the medical injection device 10.

As the proximal connection part 140 is pulled away in the radial direction due to contact with the proximal surface 124 of the first undercut 120, the opposing side of the proximal connection part 140 is flexed towards the proximal surface 128 of the second undercut 122. Due to the engagement between the opposing side of the proximal connection part 140 and the proximal surface 128, the second undercut 122 begins to assist in pulling the inner shield 30 off of the syringe tip 35 of the medical injection device 10. Once the outer shield 101 has been pulled a sufficient distance, the inner shield 30 is pulled off of the syringe tip 35 of the medical injection device 10.

All of the components of the medical injection device 10 may be constructed of any known material, and are desirably constructed of medical-grade polymers.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The application will be further described with the non-limited example below.

Example Measurement of the Pull Out Force

Measurement of the pull out force.

Needle covers including an inner shield and an outer shield of the prior art (which the outer shield does not include any undercut) or outer shield of the invention, both being previously mounted onto the tip of a glass syringe, are compared herein. The glass syringes are identical for both the needle covers of the prior art and the needle covers of the invention.

In these assays, 5 outer shields of the prior art and 5 outer shields of the invention provided with two undercuts as described in the invention are provided.

Measurements of the force needed to remove the needle cover from the syringe are carried out. The test is performed with a traction bench (500 mm/min). The method includes the steps of: placing the syringe on a holder, holding the needle cover with pneumatic jaws, and pulling the needle cover at a constant displacement rate to remove it. The force needed to pull the needle cover so as to remove it from the tip is recorded. The results are represented in the table here below.

|  | Pull out force (N) | | | | | Mean value |
| --- | --- | --- | --- | --- | --- | --- |
| Prior art needle cover | 16.30 | 17.31 | 18.30 | 17.99 | 17.49 | 17.48 |
| Invention needle cover | 9.82 | 11.76 | 13.82 | 14.14 | 12.93 | 12.49 |

The force recorded is the maximum value of the force needed to remove the needle cover recorded in function of time. Said force is the pull-out force, named "POF value". As visible in Table 1, the mean value of the POF recorded for the needle cover of the prior art is 17.48 N and the mean value of the POF recorded for the needle cover of the invention is 12.49. These values of the pull out force clearly show that the needle cover of the invention leads to a strong decrease of the pull out force compared to the known needle covers. The pull out force reduction is about 29%.

The invention claimed is:

1. A needle cover for protecting a needle mounted on a tip of a barrel of a medical injection device, wherein the tip extends from a distal end of the barrel, the needle cover comprising:
   an inner shield extending along a longitudinal axis configured to sealingly contact the tip of the barrel, and
   an outer shield surrounding at least partially the inner shield, and fixed to said inner shield, the outer shield comprising:
     a body including a first open end, a second end, and a sidewall extending between the first open end and the second end, the body defining a cavity to receive the inner shield therein;
     a first undercut defined in the sidewall adjacent the first open end of the body; and
     a second undercut defined in the sidewall adjacent the first open end of the body,
     wherein a distance from the first open end to a proximal edge of the first undercut is greater than a distance from the first open end to a proximal edge of the second undercut,
     the inner shield comprises a proximal connection part received in the first undercut and the second undercut,
   wherein during a removal of the needle cover from the medical injection device, as the outer shield is moved in the distal direction under a pulling force, the proximal end of the first undercut is configured to first contact the proximal connection part and an opposing side of the proximal connection part is configured to be flexed towards the proximal end of the second undercut, and
   wherein engagement between the proximal connection part and the proximal end of the second undercut is configured to assist in disengagement of the inner shield from the tip.

2. The needle cover of claim 1, wherein a longitudinal length of the first undercut extending from the first open end towards the second end is less than a longitudinal length of the second undercut extending from the first open end towards the second end.

3. The needle cover of claim 1, further comprising:
   a first latching tab that extends from an inner surface of the body proximate the first undercut; and
   a second latching tab that extends from the inner surface of the body proximate the second undercut.

4. The needle cover of claim 3, wherein the first latching tab has a circumferential width that is greater than a circumferential width of the second latching tab.

5. The needle cover of claim 3, wherein the first and second latching tabs comprise a proximal angled surface.

6. The needle cover of claim 1, wherein a difference between the distance from the first open end to the proximal edge of the first undercut and the distance from the first open end to the proximal edge of the second undercut is at least 1 millimeter.

7. The needle cover of claim 1, wherein the first and second undercuts are rectangular in shape.

8. The needle cover of claim 1, wherein the body defines at least one U-shaped groove on an outer surface thereof.

9. The needle cover of claim 8, wherein the U-shaped groove comprises a distal wall and a proximal wall that extend radially from the body.

10. The needle cover of claim 1, wherein a distance from the first open end to a distal surface of the first undercut is equal to a distance from the first open end to a distal surface of the second undercut.

11. The needle cover of claim 1, wherein the outer shield is fixed to the inner shield by a snap-fit connection, and the proximal connection part of the inner shield is inserted in the first and second undercuts of the outer shield to form the snap-fit connection.

12. A medical assembly, comprising:
   a medical injection device, comprising:
     a barrel defining a reservoir adapted to contain a medical composition;
     a tip extending from a distal face of the barrel, defining a fluid path extending through the tip and in fluid communication with the reservoir; and
     a needle in communication with the reservoir; and
   the needle cover according to claim 1 adapted to cover the needle.

13. The medical assembly according to claim 12, wherein the barrel and the tip of the medical injection device are made of glass.

* * * * *